(12) United States Patent
Zuhars et al.

(10) Patent No.: US 7,912,662 B2
(45) Date of Patent: Mar. 22, 2011

(54) SYSTEM AND METHOD FOR IMPROVING THE DISTORTION TOLERANCE OF AN ELECTROMAGNETIC TRACKING SYSTEM

(75) Inventors: Joel Frederick Zuhars, Haverhill, MA (US); Jason Rene Chandonnet, Tyngsboro, MA (US)

(73) Assignee: General Electric Company, Schenectady, NY (US)

( * ) Notice: Subject to any disclaimer, the term of this patent is extended or adjusted under 35 U.S.C. 154(b) by 833 days.

(21) Appl. No.: 11/859,946

(22) Filed: Sep. 24, 2007

(65) Prior Publication Data

US 2009/0082989 A1    Mar. 26, 2009

(51) Int. Cl.
*G01D 18/00* (2006.01)
*G01C 17/00* (2006.01)

(52) U.S. Cl. ........... 702/85; 600/424; 702/104; 702/150

(58) Field of Classification Search ............. 702/38, 702/75, 85, 104, 107, 150, 152; 600/407, 600/424; 324/207.21; 342/450, 463; 455/41.1; 128/897; 606/130; 343/895
See application file for complete search history.

(56) References Cited

U.S. PATENT DOCUMENTS

| | | | |
|---|---|---|---|
| 5,640,170 A | 6/1997 | Anderson | |
| 5,676,673 A | 10/1997 | Ferre et al. | |
| 5,800,352 A | 9/1998 | Ferre et al. | |
| 5,803,089 A | 9/1998 | Ferre et al. | |
| 5,873,822 A | 2/1999 | Ferre et al. | |
| 6,175,756 B1 | 1/2001 | Ferre et al. | |
| 7,015,859 B2 | 3/2006 | Anderson | |
| 7,158,754 B2 | 1/2007 | Anderson | |
| 2005/0085720 A1 | 4/2005 | Jascob et al. | |
| 2005/0107687 A1 | 5/2005 | Anderson | |
| 2005/0222793 A1* | 10/2005 | Lloyd et al. | 702/104 |
| 2006/0025677 A1 | 2/2006 | Verard | |
| 2006/0036151 A1 | 2/2006 | Ferre et al. | |
| 2006/0084867 A1 | 4/2006 | Tremblay et al. | |

\* cited by examiner

*Primary Examiner* — John H Le
(74) *Attorney, Agent, or Firm* — Kirton & McConkie; Kenneth E. Horton

(57) ABSTRACT

A system and method for improving the tolerability of metal distorters within the electromagnetic field of an electromagnetic tracking system through the use of transmission frequency optimization techniques and/or solution subset measurements.

19 Claims, 4 Drawing Sheets

SYSTEM AND METHOD FOR IMPROVING THE DISTORTION TOLERANCE OF AN ELECTROMAGNETIC TRACKING SYSTEM

BACKGROUND OF THE INVENTION

This disclosure relates generally to an electromagnetic tracking system that uses electromagnetic fields to determine the position and orientation of an object, and more particularly to a system and method for improving the distortion tolerance of an electromagnetic tracking system.

Electromagnetic tracking systems have been used in various industries and applications to provide position and orientation information relating to objects. For example, electromagnetic tracking systems may be useful in aviation applications, motion sensing applications, retail applications, and medical applications. In medical applications, electromagnetic tracking systems have been used to provide an operator (e.g., a physician, surgeon, or other medical practitioner) with information to assist in the precise and rapid positioning of a medical device or instrument located in or near a patient's body during image-guided surgery. An electromagnetic tracking system provides positioning and orientation information for a medical device or instrument with respect to the patient or a reference coordinate system. An electromagnetic tracking system provides intraoperative tracking of the precise location of a medical device or instrument in relation to multidimensional images of a patient's anatomy.

An electromagnetic tracking system uses visualization tools to provide a medical practitioner with co-registered views of a graphical representation of the medical device or instrument with pre-operative or intraoperative images of the patient's anatomy. In other words, an electromagnetic tracking system allows a medical practitioner to visualize the patient's anatomy and track the position and orientation of a medical device or instrument with respect to the patient's anatomy. As the medical device or instrument is positioned with respect to the patient's anatomy, the displayed image is continuously updated to reflect the real-time position and orientation of the medical device or instrument. The combination of the image and the representation of the tracked medical device or instrument provide position and orientation information that allows a medical practitioner to manipulate a medical device or instrument to a desired location with an accurate position and orientation.

Generally, electromagnetic tracking systems include electromagnetic transmitters and electromagnetic receivers with at least one coil or a coil array. An alternating drive current signal is provided to each coil in the electromagnetic transmitter, generating an electromagnetic field being emitted from each coil of the electromagnetic transmitter. The electromagnetic field generated by each coil in the electromagnetic transmitter induce a voltage in each coil of the electromagnetic receiver. These voltages are indicative of the mutual inductances between the coils of the electromagnetic transmitter and the coils of the electromagnetic receiver. These voltages and mutual inductances are sent to a computer for processing. The computer uses these measured voltages and mutual inductances to calculate the position and orientation of the coils of the electromagnetic transmitter relative to the coils of the electromagnetic receiver, or the coils of the electromagnetic receiver relative to the coils of the electromagnetic transmitter, including six degrees of freedom (x, y, and z measurements, as well as roll, pitch and yaw angles).

Preferably, the mutual inductances between coils of the electromagnetic transmitter and the electromagnetic receiver may be measured without inaccuracies. However, electromagnetic tracking systems are known to suffer from accuracy degradation due to electromagnetic field distortion caused by the presence of an uncharacterized metal distorter within the tracking volume or electromagnetic fields of the electromagnetic tracking system. The presence of an uncharacterized metal distorter within the tracking volume of the electromagnetic tracking system may create distortion of the electromagnetic fields of the electromagnetic tracking system. This distortion may cause inaccuracies in tracking the position and orientation of medical devices and instruments by causing inaccuracies in position and orientation calculations of the coils of the electromagnetic transmitter relative to the coils of the electromagnetic receiver, or the coils of the electromagnetic receiver relative to the coils of the electromagnetic transmitter.

Therefore, there is a need for a system and method for improving the distortion tolerance of an electromagnetic tracking system, and minimizing the effect of distortion on position and orientation calculations performed by the electromagnetic tracking system.

BRIEF DESCRIPTION OF THE INVENTION

In an exemplary embodiment, a method of improving the distortion tolerance of an electromagnetic tracking system, the method comprising calculating a plurality of position and orientation values using a plurality of different coil combinations; analyzing the plurality of position and orientation values to determine differences between the plurality of position and orientation values; and using an optimizing technique to change the operating conditions of the electromagnetic tracking system to reduce the differences between the plurality of position and orientation values.

In an exemplary embodiment, a method of improving the distortion tolerance of an electromagnetic tracking system, the method comprising calculating a plurality of position and orientation values using a plurality of different coil combinations; calculating a distortion indicator; comparing the distortion indicator to the differences between the plurality of position and orientation values; and using an optimizing technique to change the operating conditions of the electromagnetic tracking system when the distortion indicator is greater than a predetermined threshold value to reduce the differences between the plurality of position and orientation values.

In an exemplary embodiment, a method of improving the distortion tolerance of an electromagnetic tracking system, the method comprising determining a set of optimal transmitter frequencies in real-time for use by the electromagnetic tracking system; and using the set of optimal transmitter frequencies to reduce the distortion caused by a distorter within the tracking volume.

In an exemplary embodiment, a method of improving the distortion tolerance of an electromagnetic tracking system, the method comprising calculating a plurality of position and orientation values using a plurality of different transmitter frequencies; analyzing the plurality of position and orientation values to determine differences between the plurality of position and orientation values; and using an optimizing technique to change the operating conditions of the electromagnetic tracking system to reduce the differences between the plurality of position and orientation values.

In an exemplary embodiment, a method of improving the distortion tolerance of an electromagnetic tracking system, the method comprising calculating a plurality of position and orientation values using a plurality of different coil combinations; analyzing the plurality of position and orientation values to determine differences between the plurality of position and orientation values; and removing a particular coil or coils from a coil set to reduce the level of disagreement between the plurality of position and orientation values when there are multiple position and orientation values from the set and a particular coil or coils is used repeatedly in position and orientation values that are above an acceptable range of position and orientation values or above a predetermined threshold value.

Various other features, objects, and advantages of the invention will be made apparent to those skilled in the art from the accompanying drawings and detailed description thereof.

DETAILED DESCRIPTION OF THE INVENTION

Figure 1:
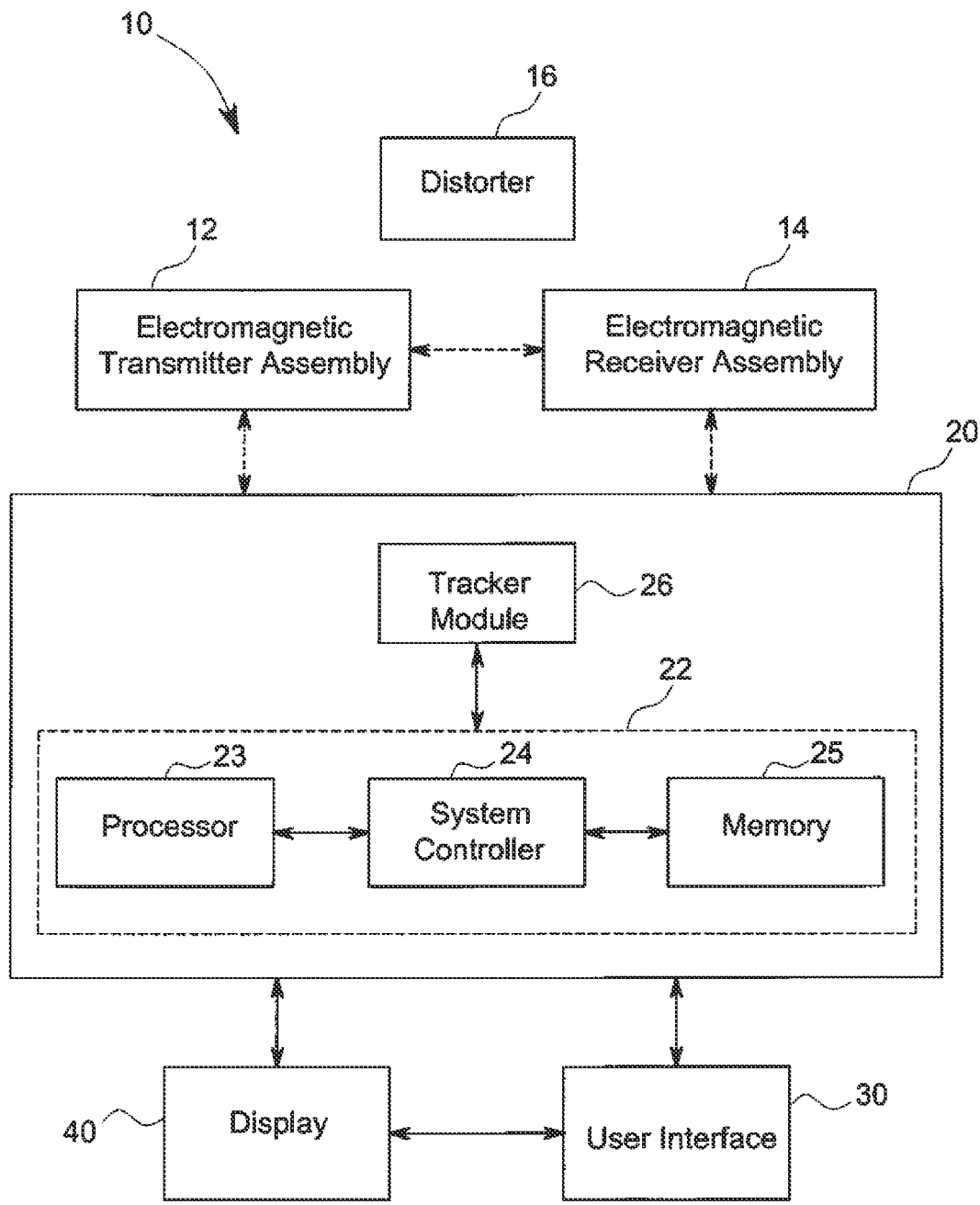
FIG. 1 is a block diagram illustrating an exemplary embodiment of an electromagnetic tracking system.

Referring now to the drawings, FIG. 1 is a block diagram illustrating an exemplary embodiment of an electromagnetic tracking system 10. The electromagnetic tracking system 10 comprises at least one electromagnetic transmitter assembly 12 with a set of one or more coils or a coil array, and at least one electromagnetic receiver assembly 14 with a set of one or more coils or a coil array. The electromagnetic tracking system 10 provides position and orientation data that spatially relate one or more coils, sets of coils, subsets of coils with one or more other coils, sets of coils, subsets of coils. Each of the coils in each set of coils or subset of coils is positioned in a fixed manner relative to each other, such as within the same housing. In an exemplary embodiment, none of the one or more coils of the electromagnetic transmitter assembly 12 transmit on the same frequency at the same time to avoid self-interference.

FIG. 1 also illustrates at least one distorter 16 within the tracking volume of the electromagnetic tracking system 10. The at least one distorter 16 may include field-distorting electrically-conductive material. In an exemplary embodiment, the at least one distorter 16 may include any ferrous metal object. This at least one distorter 16 may distort the electromagnetic fields being generated by the one or more coils of the electromagnetic transmitter assembly 12, and thus skew the measurements of the position and orientation of the one or more coils of the electromagnetic receiver assembly 14 relative to the one or more coils of the electromagnetic transmitter assembly 12. The at least one distorter 16 may also skew the measurements of the position and orientation of the one or more coils of the electromagnetic transmitter assembly 12 relative to the one or more coils of the electromagnetic receiver assembly 14.

The electromagnetic tracking system 10 further comprises a tracker workstation 20 coupled to and receiving data from the at least one electromagnetic transmitter assembly 12 and the at least one electromagnetic receiver assembly 14, a user interface 30 coupled to the tracker workstation 20, and a display 40 for visualizing imaging and tracking data. The tracker workstation 20 includes a tracking system computer 22 and a tracker module 26. The tracking system computer 22 includes at least one processor 23, a system controller 24 and memory 25.

In an exemplary embodiment, the at least one electromagnetic transmitter assembly 12 may be a battery-powered wireless transmitter assembly, a passive transmitter assembly, or a wired transmitter assembly. In an exemplary embodiment, the at least one electromagnetic receiver assembly 14 may be a battery-powered wireless receiver assembly, a passive receiver assembly, or a wired receiver assembly.

In an exemplary embodiment, the at least one electromagnetic transmitter assembly 12 may be attached to a medical device or instrument to be tracked and the at least one electromagnetic receiver assembly 14 is positioned within or near the area of interest.

In an exemplary embodiment, the at least one electromagnetic receiver assembly 14 may be attached to a medical device or instrument to be tracked and the at least one electromagnetic transmitter assembly 12 is positioned within or near the area of interest.

In an exemplary embodiment, the tracker module 26 may include drive circuitry configured to provide a drive current to each coil of the at least one electromagnetic transmitter assembly 12. By way of example, a drive current may be supplied by the drive circuitry to energize a coil of the at least one electromagnetic transmitter assembly 12, and thereby generate an electromagnetic field that is detected by a coil of the at least one electromagnetic receiver assembly 14. The drive current may be comprised of a periodic waveform with a given frequency (e.g., a sine wave, cosine wave or other periodic signal). The drive current supplied to a coil will generate an electromagnetic field at the same frequency as the drive current. The electromagnetic field generated by the one or more coils of the electromagnetic transmitter assembly 12 induces a voltage indicative of the mutual inductance in the one or more coils of the electromagnetic receiver assembly 14. In an exemplary embodiment, the tracker module 26 may include receiver data acquisition circuitry for receiving voltage and mutual inductance data from the electromagnetic receiver assembly 14.

In an exemplary embodiment, the tracking system computer 22 may include at least one processor 23, such as a digital signal processor, a CPU, or the like. The processor 23 may process measured voltage and mutual inductance data from the electromagnetic receiver assembly 14 to track the position and orientation of the electromagnetic transmitter assembly 12 or the electromagnetic receiver assembly 14.

The processor 23 may implement any suitable algorithm(s) to use the measured voltage signal indicative of the mutual inductance to calculate the position and orientation of the electromagnetic receiver assembly 14 relative to the electromagnetic transmitter assembly 12, or the electromagnetic transmitter assembly 12 relative to the electromagnetic receiver assembly 14. For example, the processor 23 may use ratios of mutual inductance between each coil of the electromagnetic receiver assembly 14 and each coil of the electromagnetic transmitter assembly 12 to triangulate the relative positions of the coils. The processor 23 may then use these relative positions to calculate the position and orientation of the electromagnetic transmitter assembly 12 or the electromagnetic receiver assembly 14.

In an exemplary embodiment, the tracking system computer 22 may include a system controller 24. The system controller 24 may control operations of the electromagnetic tracking system 10.

In an exemplary embodiment, the tracking system computer 22 may include memory 25, which may be any processor-readable media that is accessible by the components of the tracker workstation 20. In an exemplary embodiment, the memory 25 may be either volatile or non-volatile media. In an exemplary embodiment, the memory 25 may be either removable or non-removable media. Examples of processor-readable media may include (by way of example and not limitation): RAM (Random Access Memory), ROM (Read Only Memory), registers, cache, flash memory, storage devices, memory sticks, floppy disks, hard drives, CD-ROM, DVD-ROM, network storage, and the like.

In an exemplary embodiment, the user interface 30 may include devices to facilitate the exchange of data and workflow between the system and the user. In an exemplary embodiment, the user interface 30 may include a keyboard, a mouse, a joystick, buttons, a touch screen display, or other devices providing user-selectable options, for example. In an exemplary embodiment, the user interface 30 may also include a printer or other peripheral devices.

In an exemplary embodiment, the display 40 may be used for visualizing the position and orientation of a tracked object with respect to a processed image from an imaging system.

Notwithstanding the description of the exemplary embodiment of the electromagnetic tracking system 10 illustrated FIG. 1, alternative system architectures may be substituted without departing from the scope of the invention.

The set of one or more coils of the electromagnetic transmitter and receiver assemblies 12, 14 may be built with various coil architectures. The one or more coils of the electromagnetic transmitter assembly 12 may be a single coil, an industry-standard-coil-architecture (ISCA) type coil, a pair of ISCA type coils, multiple coils, or a coil array of one or more coils. The one or more coils of the electromagnetic receiver assembly 14 may be a single coil, an ISCA type coil, a pair of ISCA type coils, multiple coils, or a coil array of one or more coils.

ISCA type coils are defined as three approximately collocated, approximately orthogonal, and approximately dipole coils. Therefore, ISCA electromagnetic transmitter and receiver assemblies would include three approximately collocated, approximately orthogonal, and approximately dipole coils for the transmitter assembly and three approximately collocated, approximately orthogonal, and approximately dipole coils for the receiver assembly. In other words, an ISCA configuration for electromagnetic transmitter and receiver assemblies would include a three-axis dipole coil transmitter and a three-axis dipole coil receiver. In the ISCA configuration, the transmitter coils and the receiver coils are configured such that the three coils (i.e., coil trios) exhibit the same effective area, are oriented orthogonally to one another, and are centered at the same point.

In an exemplary embodiment, the coil array of one or more coils may be configured with multiple coils capable of providing multiple electromagnetic fields of varying magnitude and direction. By way of example, the coil array of one or more coils may be implemented with three concentric and orthogonal dipole coils (coil trios) and thus capable of generating electromagnetic fields in three planes (i.e., x, y and z planes).

In an exemplary embodiment, the set of one or more coils of the at least one electromagnetic transmitter assembly 12 may be characterized as single dipole coils and emit magnetic fields when a current is passed through the one or more coils. Those skilled in the art will appreciate that multiple electromagnetic field generating coils may be used in coordination to generate multiple electromagnetic fields. Similar to the at least one electromagnetic transmitter assembly 12, the set one or more coils of the at least one electromagnetic receiver assembly 14 may be characterized as single dipole coils and detect the electromagnetic fields emitted by the at least one electromagnetic transmitter assembly 12. When a current is applied to the coils of the at least one electromagnetic transmitter assembly 12, the electromagnetic fields generated by the coils may induce a voltage into each coil of the at least one electromagnetic receiver assembly 14. The induced voltage is indicative of the mutual inductance between the one or more coils of the at least one electromagnetic transmitter assembly 12. Thus, the induced voltage across each coil of the at least one electromagnetic receiver assembly 14 is detected and processed to determine the mutual inductance between each coil of the at least one electromagnetic transmitter assembly 12 and each coil of the at least one electromagnetic receiver assembly 14.

In an exemplary embodiment, the set of one or more coils of the electromagnetic transmitter and receiver assemblies 12, 14 are either precisely manufactured or precisely characterized during manufacture to obtain mathematical models of the set of one or more coils in the electromagnetic transmitter and receiver assemblies 12, 14. From the electromagnetic field measurements and mathematical models of the set of one or more coils, the position and orientation of the at least one electromagnetic receiver assembly 14 with respect to the at least one electromagnetic transmitter assembly 12 may be determined. Alternatively, the position and orientation of the at least one electromagnetic transmitter assembly 12 with respect to the at least one electromagnetic receiver assembly 14 may be determined.

Figure 2:
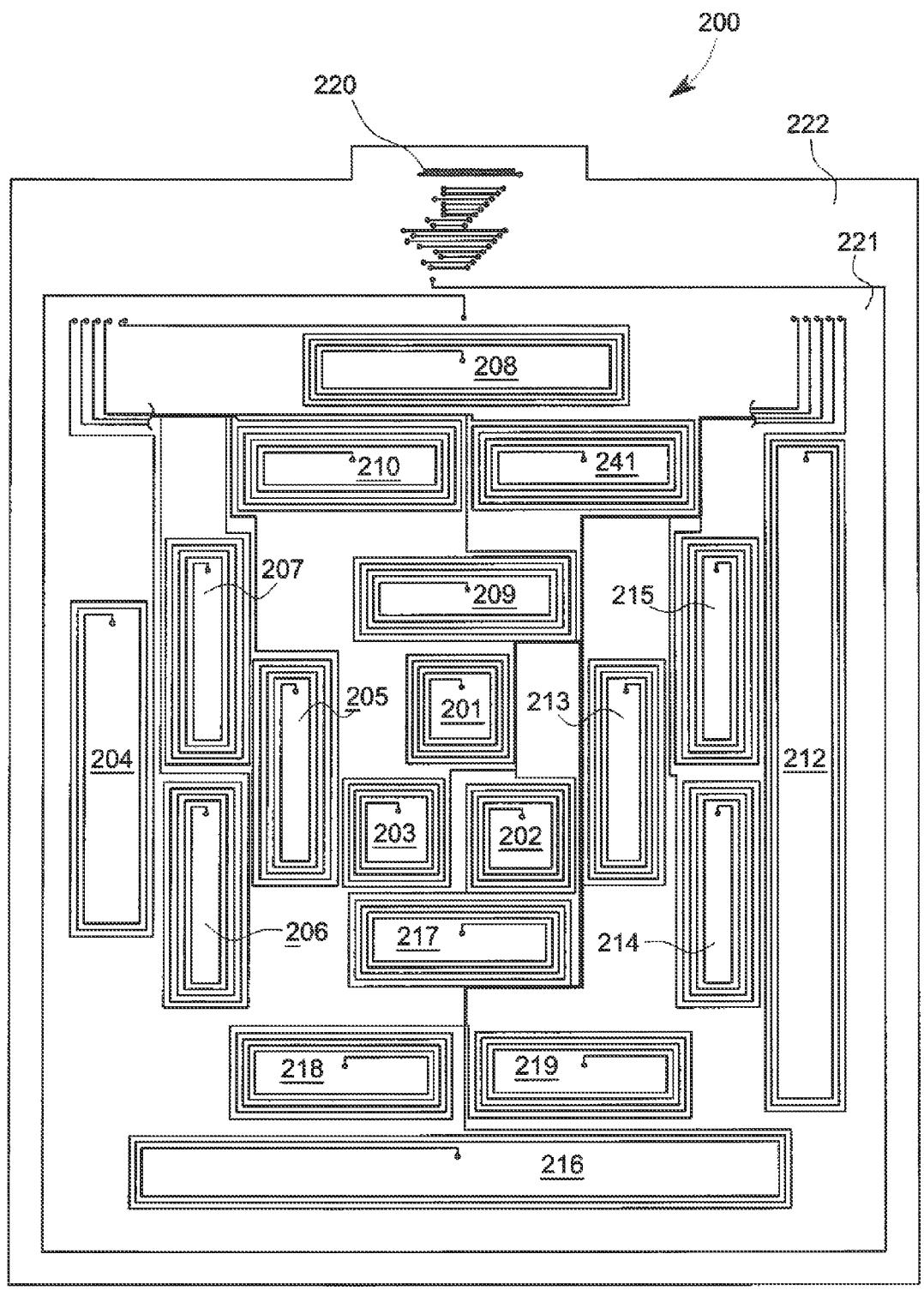
FIG. 2 is a schematic diagram illustrating an exemplary embodiment of an electromagnetic transmitter or receiver coil array for an electromagnetic tracking system.

FIG. 2 is a schematic diagram illustrating an exemplary embodiment of an electromagnetic transmitter or receiver coil array 200 for an electromagnetic tracking system. It is well known by the electromagnetic principle of reciprocity, that a description of a coil's properties as a transmitter can also be used to understand the coil's properties as a receiver. Therefore, this example coil array 200 may be used as a transmitter or a receiver.

This example coil array 200 is formed by a plurality of flat coils of straight conductor traces forming square or rectangularly-shaped spiral coils on a printed circuit board (PCB) 222. The spiral coils are preferably copper traces with spaces in-between. The spiral coils may be single-sided or double-sided on the PCB 222. The PCB 222 may be a two-sided single layer or multi-layer PCB. The PCB 222 includes at least one layer with conductors on one or both sides, or even on inner layers, and including a plurality of conductor through holes 220 for mounting a connector to the PCB 222. The PCB 222 may also include a plurality of additional conductor through holes within the spiral coils and other locations of the PCB. The PCB 222 may be made of a material that is rigid or flexible.

In an exemplary embodiment, the coil array PCB 222 includes twelve (12) separate coils, plus a calibration coil. Four of the coils are single spiral coils 201, 202, 203 and 221. Eight of the coils are spiral coil pairs 204-212, 207-215, 206-214, 205-213, 211-219, 208-216, 210-218, and 209-217. The second spiral coil in each pair is wound in the opposite direction from the first spiral coil to form electromagnetic fields that are parallel to the plane of the PCB 222. The spiral coils are arranged to generate electromagnetic fields and gradients in all three axes (x, y, and z) directions at a "sweet spot" located above at least one side of the PCB 222. The x and y directions are in the plane of the PCB 222. The z direction is perpendicular to the plane of the PCB 222.

A first coil (coil 1) comprises first spiral coil 204 and second spiral coil 212. A second coil (coil 2) comprises first spiral coil 207 and second spiral coil 215. A third coil (coil 3) comprises first spiral coil 206 and second spiral coil 214. A fourth coil (coil 4) comprises first spiral coil 205 and second spiral coil 213. A fifth coil (coil 5) comprises first spiral coil 211 and second spiral coil 219. A sixth coil (coil 6) comprises first spiral coil 208 and second spiral coil 216. A seventh coil (coil 7) comprises first spiral coil 210 and second spiral coil 218. An eighth coil (coil 8) comprises first spiral coil 209 and second spiral coil 217. A ninth coil (coil 9) comprises spiral coil 202. A tenth coil (coil 10) comprises spiral coil 203. An eleventh coil (coil 11) comprises spiral coil 201. A twelfth coil (coil 12) comprises spiral coil 221. Spiral coil 221 (coil 12) is located around the edges or periphery of PCB 222 and thus surrounds all the other spiral coils.

In an exemplary embodiment, the PCB 222 may include a calibration coil. The calibration coil is a thirteenth coil of one turn, laid out to provide a known small mutual inductance to each of the other coils.

In an exemplary embodiment, the PCB 222 does not include coils with curved traces. Electromagnetic fields may be more precisely calculated with coils having straight-line segments.

Figure 3:
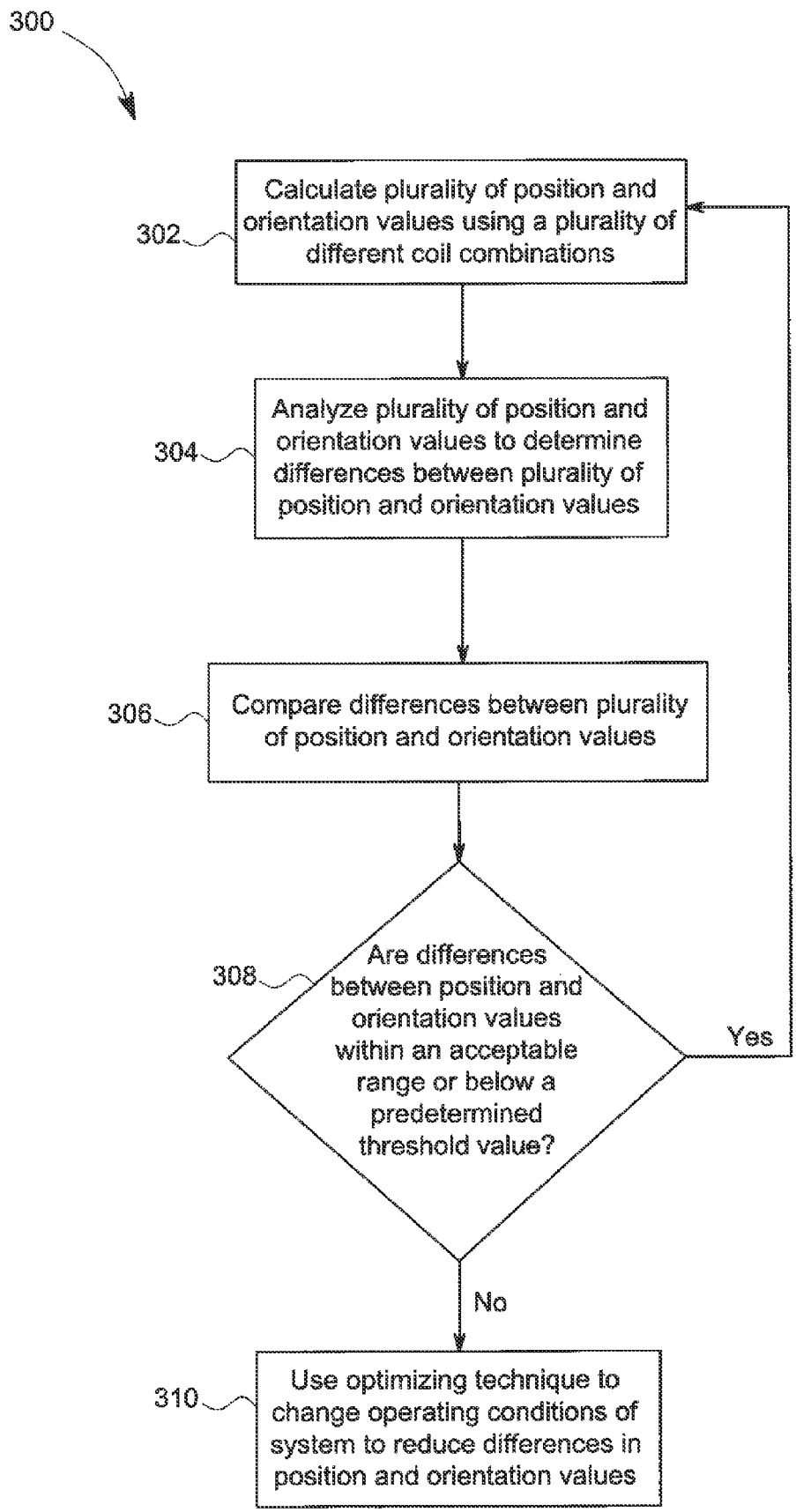
FIG. 3 is a flow diagram illustrating an exemplary embodiment of a method for improving the distorter tolerance of an electromagnetic tracking system.

FIG. 3 is a flow diagram illustrating an exemplary embodiment of a method 300 for improving the distorter tolerance of an electromagnetic tracking system. The method 300 may be performed on an electromagnetic tracking system having at least one transmitter assembly with a set of one or more coils or a coil array and at least one receiver assembly with a set of one or more coils or a coil array for position and orientation tracking of the at least one receiver assembly relative to the at least one transmitter assembly, or vice versa according to any suitable method or system. The method 300 may be performed by at least one computer program or algorithm running on a tracking system computer.

The method 300 begins by calculating a plurality of position and orientation values of the receiver coils relative to the transmitter coils using a plurality of different coil combinations at step 302. For example, the electromagnetic transmitter assembly may include a single electromagnetic field generating coil and the electromagnetic receiver assembly may include a set of 12 receiver coils. Data from all 12 receiver coils may be used in calculating a position and orientation value. However, additional position and orientation values may also be calculated for a plurality of coil subsets, like coils 1-6, coils 7-12, coils 1, 3, 5, 7, 9, and 11, coils 1-8, and so on. Position and orientation values may be calculated for each coil, set of coils, or subset of coils. This results in a plurality of position and orientation values being available for analysis. This example discloses the use of a single coil transmitter and a 12 coil array receiver. However, the electromagnetic transmitter assembly may include any number of transmitter coils and the electromagnetic receiver assembly may include any number of receiver coils.

In order to obtain a unique solution for both position and orientation concurrently between two or more coils, sets of coils or subsets of coils, it is necessary to define coordinate reference frames relative to each coil, set of coils or subset of coils and concurrently determine the values of six independent degrees of freedom of motion (x, y, z, roll, pitch, and yaw) between the coils, sets of coils or subsets of coils. Fewer than six degrees of freedom may result in an effectively determined solution, if not unique, due to the specific intended use of the information, which may include taking advantage of physical device symmetries in some cases, thereby rendering all potentially unique solutions as being effectively the same solution. More than six degrees of freedom will result in an overdetermined system where multiple, possibly different, unique solutions will be available for the position and orientation between the coils, sets of coils or subsets of coils. In other words, if a position and orientation solution is defined by the six degrees of freedom of motion parameters (x, y, z, roll, pitch, and yaw), an overdetermined system will yield multiple, possibly different, yet equally valid results for some or all of the parameters, depending on how the available information is used.

In the case of an overdetermined system, such as when the quantity of transmitter and/or receiver coils within a particular coil set or subset pairing is more than the minimum necessary to determine a unique position and orientation solution for the pairing, it is possible to generate a series of position and orientation solutions by using some or all of the permutations of coil sets or subsets within the set or subset pairing. Each solution in this series could be based on either exactly the minimum six degrees of freedom required for a particular unique solution, or any amount of degrees of freedom between the minimum six and the full available set, including the solution generated from the full set.

Continuing with the method 300 at step 304, the plurality of position and orientation values are analyzed to determine the degree of disagreement or differences between the plurality of position and orientation values, which should all theoretically be the same with no differences. Differences to some degree beyond a normal amount can be indicative of the presence of a distorter within the electromagnetic field(s) of the electromagnetic tracking system.

Either the level of disagreement, or a threshold event of when the disagreement level exceeds a predetermined threshold value may be used as a driver for an optimization technique, which attempts to change the operating conditions of the system to reduce the disagreement level. This level of disagreement or the threshold event may be used as a distortion indicator to indicate the presence of a distorter within the electromagnetic field(s) of the electromagnetic tracking system. The distortion indicator is based on the level of disagreement or relative difference between the plurality of position and orientation values. Theoretically, the level of disagreement or relative difference between the plurality of position and orientation values is zero, so theoretically, the distortion indicator would be zero. The distortion indicator has two modes of operation. This disclosure contemplates both modes of operation of the distortion indicator, either separately or together.

In an exemplary embodiment, in a first mode, the distortion indicator is a continuous measure of the level of disagreement or relative difference between the plurality of position and orientation values, where the indicator might feedback into the system, and triggers an error condition when the distortion indicator is outside of an acceptable range. In other words, is the level of disagreement in position and orientation values or the distortion indicator above an acceptable level? If yes, then an optimizing technique is used to change the operating conditions of the system to reduce the disagreement level.

In an exemplary embodiment, in a second mode, the distortion indicator is binary measure of the level of disagreement or relative difference between the plurality of position and orientation values, where some predetermined threshold value, greater than zero, is compared to the distortion indicator, and triggers an error condition when the distortion indicator is above the predetermined threshold value. In other words, are differences in position and orientation values or the distortion indicator above a predetermined threshold value? If yes, then an optimizing technique is used to change the operating conditions of the system to reduce the disagreement level.

The distortion indicator is a number with a numerical value. In an exemplary embodiment, the distortion indicator may have two values, one for position and one for orientation, each of which is analyzed separately, to deal with the fact that position units are in millimeters (mm) and orientation units are in radians or degrees. An error condition occurs when there is a difference or disagreement in position and orientation values using different coils, sets of coils or subsets of coils, which should ideally result in the same answer, or were more than a predetermined threshold value. For example, position and orientation values may be different if a distorter is closer to one coil, set of coils or subset of coils than another coil, set of coils or subset of coils. Also, the position and orientation values may be different for different distorters.

At step 306, compare differences between the plurality of position and orientation values. This step 306 may include calculating the distortion indicator as an indicator of the level of disagreement or relative difference between the plurality of position and orientation values.

At step 308, are the differences between position and orientation values within an acceptable range or below a predetermined threshold value? This step 308 may include determining if the distortion indicator is within an acceptable range or below a predetermined threshold value? If the plurality of position and orientation values or the distortion indicators are not within the acceptable range nor below the predetermined threshold value, then an optimizing technique is used to change the operating conditions of the electromagnetic tracking system to reduce the differences in the position and orientation values at step 310. In other words, if the position and orientation value changes are considered significant, than an optimization technique is used to compensate for the distortion at step 310. If the plurality of position and orientation values or the distortion indicators are within the acceptable range or below the predetermined threshold value, then continue with the tracking procedure while continuously checking for a distorter in the tracking volume (electromagnetic field(s), going back to 302 until the procedure is completed.

This method 300 detects the presence of a distorter within the electromagnetic field(s), then adjusts the operating parameters of the system in real-time to compensate for or reduce the effect of the distorter on system performance.

In an exemplary embodiment, a plurality of position and orientation values are calculated using a plurality of different coil combinations. A comparison is made of all permutations of position and orientation value calculations made given the total number of coils and different coil combinations available. If the difference between all permutations of position and orientation value comparisons is greater than a normal disagreement level or greater than a predetermined threshold value, then there may be a distorter present (distortion indicator may be above a predetermined threshold value) in the tracking volume (within the electromagnetic field(s)), and an optimization technique is provided to improve the distortion tolerance of the electromagnetic tracking system. If the difference between all permutations of position and orientation value comparisons is not greater than a normal disagreement level or not greater than a predetermined threshold value, then there may not be a distorter present (distortion indicator may be below a predetermined threshold value) in the tracking volume (within the electromagnetic field(s)), and the tracking procedure may continue as normal.

When performing the plurality of position and orientation value comparisons, if there is a particular coil or coils that are used repeatedly in position and orientation calculations that result in position and orientation values that are above a normal disagreement level or greater than a predetermined threshold value, then those position and orientation values are removed from the other position and orientation values to reduce the level of disagreement between position and orientation values and reduce the distortion caused by a possible distorter within the tracking volume. For example, if there are 12 coils and the most disagreeable position and orientation values are from the coil combinations 1, 2, 3, 4, 5, 10 and 4, 5, 6, 7, 8, 10 and 7, 8, 9, 10, 11, 12, then all position and orientation values involving coil 10 should be removed, since coil 10 may be near the distorter.

Figure 4:
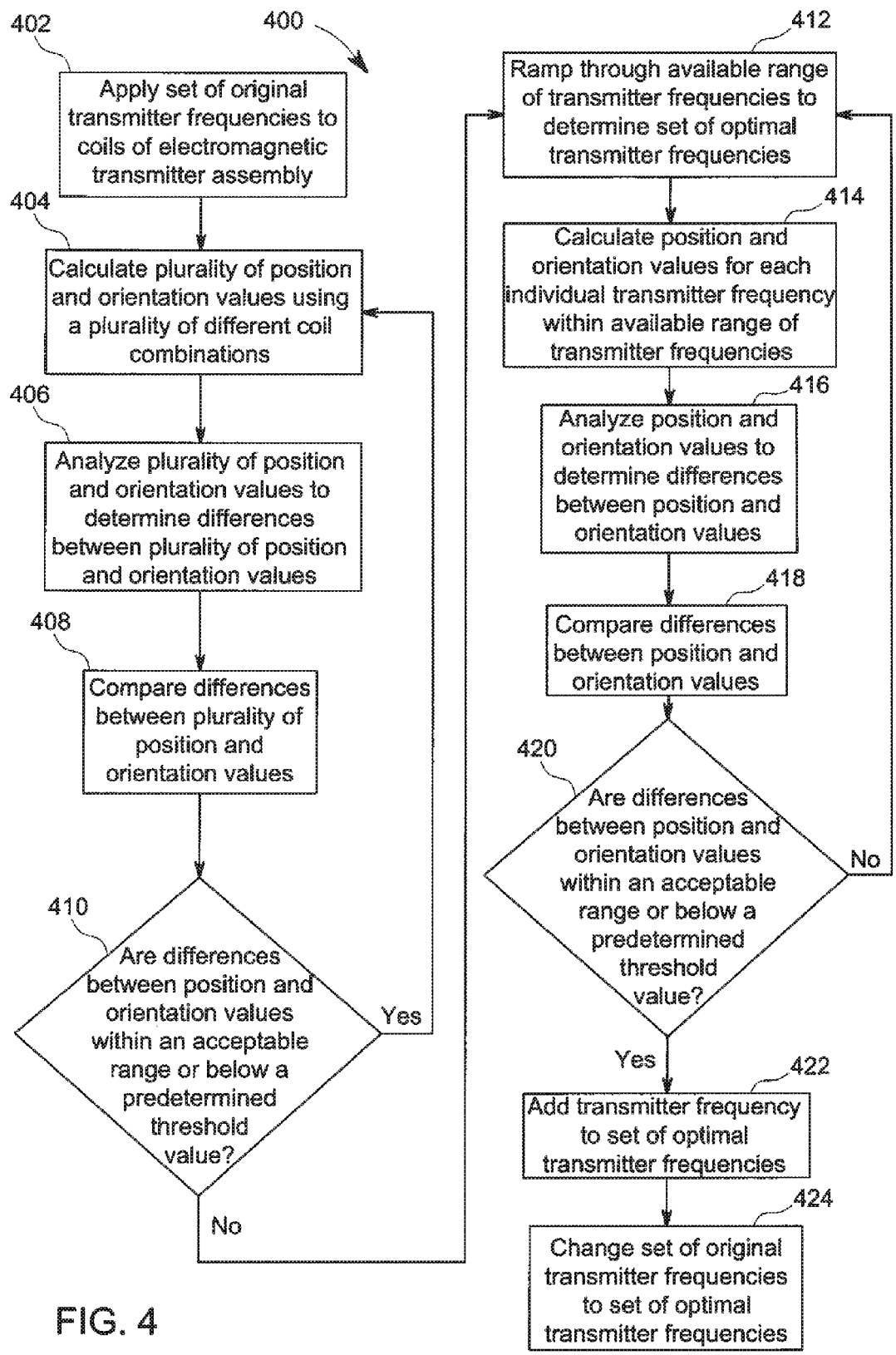
FIG. 4 is a flow diagram illustrating an exemplary embodiment of a method for improving the distorter tolerance of an electromagnetic tracking system.
Figure 2:
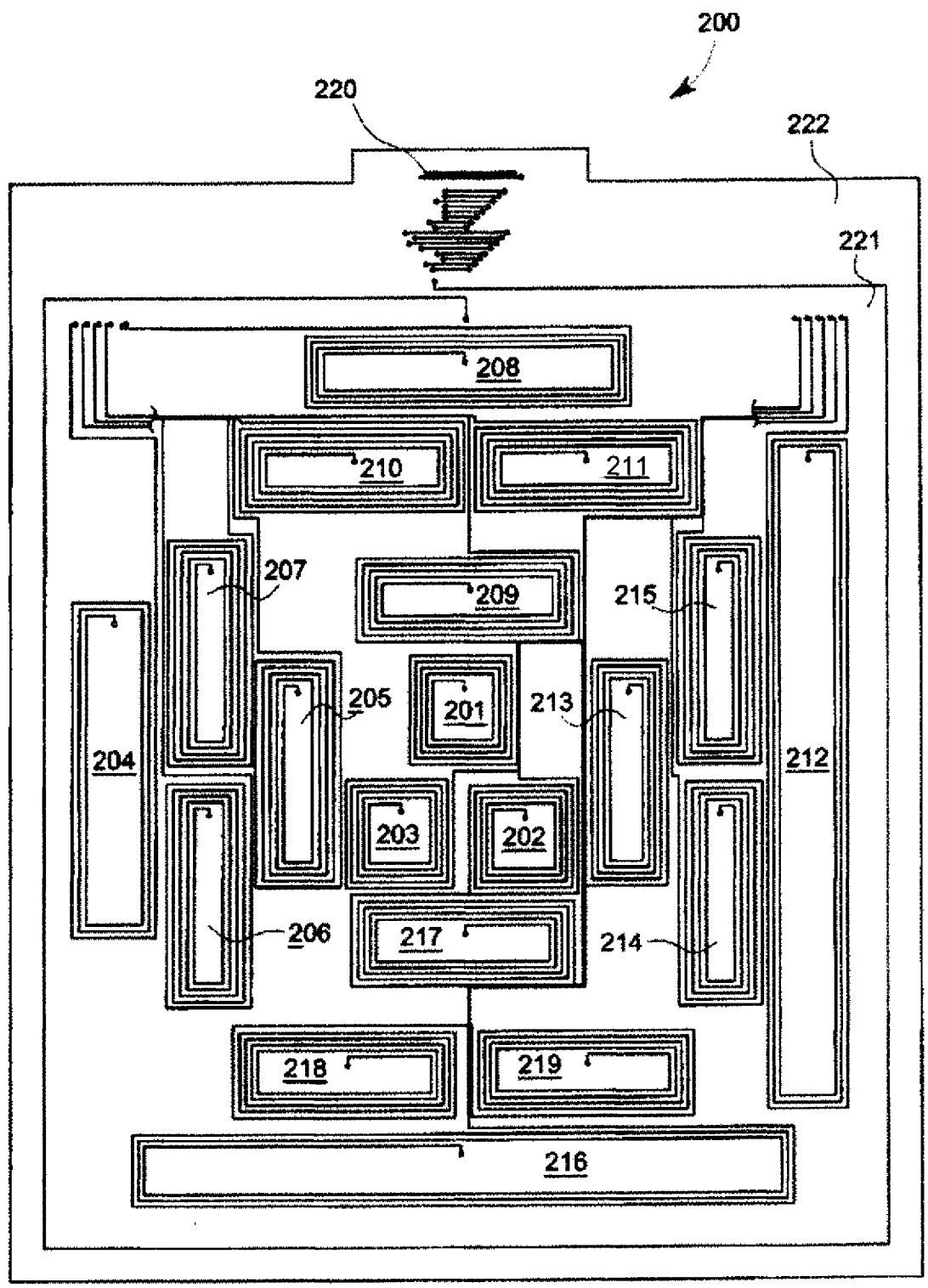
Figure 4:
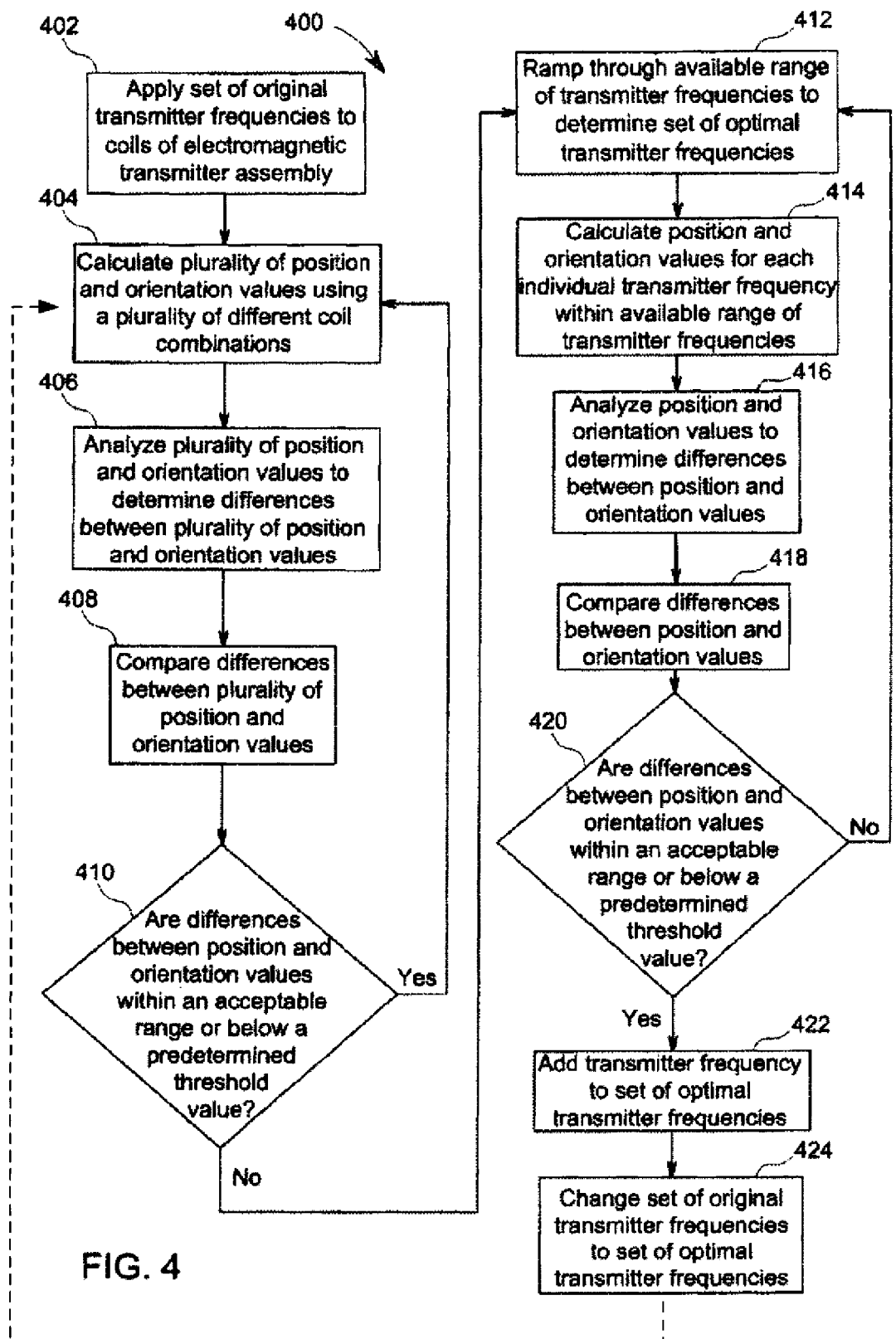

FIG. 4 is a flow diagram illustrating an exemplary embodiment of a method 400 for improving the distorter tolerance of an electromagnetic tracking system. The method 400 may be performed on an electromagnetic tracking system having at least one transmitter assembly with a set of one or more coils or a coil array and at least one receiver assembly with a set of one or more coils or a coil array for position and orientation tracking of the at least one receiver assembly relative to the at least one transmitter assembly, or vice versa according to any suitable method or system. The method 300 may be performed by at least one computer program or algorithm running on a tracking system computer.

The method 400 begins by applying a set of original transmitter frequencies to the set of one or more coils of the electromagnetic transmitter assembly at step 402.

The method continues at step 404 by calculating a plurality of position and orientation values of the receiver coils relative to the transmitter coils using a plurality of different coil combinations. For example, the electromagnetic transmitter assembly may include at least one electromagnetic field generating coil and the electromagnetic receiver assembly may include a plurality of receiver coils. Data from all of the receiver coils may be used in calculating a position and orientation value. However, additional position and orientation values may also be calculated for a plurality of different coils, sets of coils or subsets of coils. This results in a plurality of position and orientation values being available for analysis.

At step 406, the plurality of position and orientation values are analyzed to determine the degree of disagreement or differences between the plurality of position and orientation values, which should all theoretically be the same with no differences. Differences to some degree beyond a normal amount can be indicative of the presence of a distorter within the electromagnetic field(s) of the electromagnetic tracking system.

At step 408, compare differences between the plurality of position and orientation values. This step 408 may include calculating the distortion indicator as an indicator of the level of disagreement or relative difference between the plurality of position and orientation values.

At step 410, are the differences between position and orientation values within an acceptable range or below a predetermined threshold value? This step 410 may include determining if the distortion indicator is within an acceptable range or below a predetermined threshold value? If the plurality of position and orientation values or the distortion indicators are not within the acceptable range nor below the predetermined threshold value, then ramp through the available range of transmitter frequencies, one by one, to determine a set of optimal transmitter frequencies at step 412. In other words, if the position and orientation value changes are considered significant, than the transmitter frequencies are changed to reduce distortion in the electromagnetic tracking system. If the plurality of position and orientation values or the distortion indicators are within the acceptable range or below the predetermined threshold value, then continue with the tracking procedure while continuously checking for a distorter in the tracking volume (electromagnetic field(s)), going back to 404 until the procedure is completed.

It is generally known that distorters made from different types of metals will distort the electromagnetic field of an electromagnetic tracking system more or less depending on the transmitter frequencies used by electromagnetic the tracking system. This implies that a change in the set of transmitter frequencies used may allow for improved distortion tolerance of the particular type of metal present at a particular time.

Given that the type or types of metal present is not typically known before using the electromagnetic tracking system, and may change at any time, an optimal set of transmitter frequencies will not typically be known before using the electromagnetic tracking system, and will ideally be computed and changed in real-time during system use.

The method 400 continues at step 414 by calculating position and orientation values for each individual transmitter frequency within the available range of transmitter frequencies.

At step 416, the position and orientation values for each transmitter frequency are analyzed to determine the degree of disagreement or differences between the plurality of position and orientation values, which should all theoretically be the same with no differences. Differences to some degree beyond a normal amount can be indicative of the presence of a distorter within the electromagnetic field(s) of the electromagnetic tracking system.

At step 418, compare differences between the plurality of position and orientation values. This step 418 may include calculating the distortion indicator as an indicator of the level of disagreement or relative difference between the plurality of position and orientation values.

At step 420, are the differences between position and orientation values within an acceptable range or below a predetermined threshold value? This step 420 may include determining if the distortion indicator is within an acceptable range or below a predetermined threshold value? If the plurality of position and orientation values or the distortion indicators are not within the acceptable range nor below the predetermined threshold value, then continue ramping through the available range of transmitter frequencies, one by one, to determine a set of optimal transmitter frequencies at step 412. If the plurality of position and orientation values or the distortion indicators are within the acceptable range or below the predetermined threshold value, then add the transmitter frequency to the set of optimal transmitter frequencies and continue with the tracking procedure using the set of optimal transmitter frequencies while continuously checking for a distorter in the tracking volume (electromagnetic field (s), going back to 404 until the procedure is completed.

This method 400 discloses the real-time determination of an optimal set of transmitter frequencies and the ability of the system to change the set of transmission frequencies used by an electromagnetic tracking system to the optimal set of transmitter frequencies while the system is in use as a means of improving the tolerability of distorters within the electromagnetic field(s).

The following methods are contemplated for inclusion within the scope of this disclosure, but these method descriptions are intended to be illustrative in nature, and are not intended to limit the scope of the claims.

In an exemplary embodiment, whenever system accuracy is detected as having been substantially degraded by any means, which may or may not include a distortion indicator, the transmission frequencies used by the system can be ramped through the available range, and the distortion indicator can be computed at each individual frequency. The system may then continue operation using the set of frequencies that correspond to the lowest distortion indicator levels.

In an exemplary embodiment, the distortion indicator may be computed continuously, and the frequency set can be changed arbitrarily or based on a preset pattern, such as an incremental pattern with wrap around, within the available frequency range whenever the distortion indicator is greater than a predetermined threshold value until a usable frequency set is found. The predetermined threshold value may be either fixed or determined via a pre-scan of the frequency range on system startup, or some other means. The initial frequency set to use could be based on the expected environmental conditions or usage scenario. The need for changes from the initial frequency set could be used as an indicator of possible site-specific deviations from expected usage.

In an exemplary embodiment, multiple transmission frequencies may be used for each coil concurrently, i.e., the number of frequencies used is a multiple of the number of transmitting coils. The distortion indicator may be computed for each frequency or frequency set in use at the same time, and the solution tied to the best distortion indicator level can be selected for use each time. Note that the solution used may be the one tied to the full set of coil data, or some combination of solutions from the individual coils, sets of coils or subsets of coils.

In an exemplary embodiment, when the distortion indicator is computed, it may be recomputed prior to use with one of the above methods based on a subset of the position and orientation solution set after removing one or more solutions from the solution set based on an alternative distortion indicator, such as having all but one of the solutions close in agreement, resulting in the one being removed. This could result in the optimized usage of the available electromagnetic field space itself, if a distorter is affecting only a particular coil, set of coils or subset of coils by being present in only one part of a potentially distributed electromagnetic field.

In an exemplary embodiment, all uses of the distortion indicator above may alternatively be performed using different or a combination of accuracy degradation measures to improve overall performance. Alternative measures for detecting electromagnetic field distortion may include a goodness-of-fit indicator used in conjunction with frequency ramping methods, which derives a measure of accuracy degradation from a comparison between measured and modeled results for position and orientation at a particular frequency. Goodness-of-fit is a measure of how well the fitted position and orientation match the measured mutual inductance.

This method 400 detects the presence of a distorter within the electromagnetic field(s) by calculating a plurality of position and orientation values using a plurality of different coil combinations, then adjusts the operating parameters of the system in real-time by changing transmitter frequencies being used to compensate for or reduce the effect of the distorter on system performance.

In an exemplary embodiment, a plurality of position and orientation values are calculated using a plurality of different transmitter frequencies. A comparison is made of all permutations of position and orientation value calculations made given the total number of different transmission frequencies available. If the difference between all permutations of position and orientation value comparisons is greater than a normal disagreement level or greater than a predetermined threshold value, then there may be a distorter present (distortion indicator may be above a predetermined threshold value) in the tracking volume (within the electromagnetic field(s)), and an optimization technique is provided to improve the distortion tolerance of the electromagnetic tracking system. If the difference between all permutations of position and orientation value comparisons is not greater than a normal disagreement level or not greater than a predetermined threshold value, then there may not be a distorter present (distortion indicator may be below a predetermined threshold value) in the tracking volume (within the electromagnetic field(s)), and the tracking procedure may continue as normal.

In an exemplary embodiment, a plurality of position and orientation values are calculated using a plurality of different coil combinations and a plurality of different transmitter frequencies. A comparison is made of all permutations of position and orientation value calculations made given the total number of different coil combinations available and different transmitter frequencies available. If the difference between all permutations of position and orientation value comparisons is greater than a normal disagreement level or greater than a predetermined threshold value, then there may be a distorter present (distortion indicator may be above a predetermined threshold value) in the tracking volume (within the electromagnetic field(s)), and an optimization technique is provided to improve the distortion tolerance of the electromagnetic tracking system. If the difference between all permutations of position and orientation value comparisons is not greater than a normal disagreement level or not greater than a predetermined threshold value, then there may not be a distorter present (distortion indicator may be below a predetermined threshold value) in the tracking volume (within the electromagnetic field(s)), and the tracking procedure may continue as normal.

All of these methods, alternative combinations of these methods, and similar methods are claimed as part of this disclosure.

Several embodiments are described above with reference to drawings. These drawings illustrate certain details of exemplary embodiments that implement the systems, methods and computer programs of this disclosure. However, the drawings should not be construed as imposing any limitations associated with features shown in the drawings. This disclosure contemplates methods, systems and program products on any machine-readable media for accomplishing programmed operations. As noted above, certain embodiments may be implemented using an existing computer processor, or by a special purpose computer processor incorporated for this or another purpose, or by a hardwired system.

As noted above, certain embodiments within the scope of included program products comprise machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Certain embodiments described in the context of method steps may be implemented by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Certain embodiments may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the system might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

While the invention has been described with reference to various embodiments, those skilled in the art will appreciate that certain substitutions, alterations and omissions may be made to the embodiments without departing from the spirit of the invention. Accordingly, the foregoing description is meant to be exemplary only, and should not limit the scope of the disclosure as set forth in the following claims.

What is claimed is:

1. A method of improving a distortion tolerance of an electromagnetic tracking system, the method comprising:
   using a plurality of coil combinations to calculate a plurality of position and orientation values;
   using a computing device to analyze the plurality of position and orientation values to determine differences between the plurality of position and orientation values and removing the position and orientation values that are above an acceptable range or that are above a predetermined threshold value; and
   using an optimizing technique to change the operating conditions of the electromagnetic tracking system to reduce the differences between the plurality of position and orientation values.

2. The method of claim 1, wherein the optimizing technique is changing the transmitter frequencies to reduce the differences between the plurality of position and orientation values.

3. The method of claim 1, further comprising ramping through an available range of transmitter frequencies to determine a set of optimal transmitter frequencies to reduce the differences between the plurality of position and orientation values.

4. The method of claim 3, applying the set of optimal transmitter frequencies to a transmitter assembly of the electromagnetic tracking system to reduce the differences between the plurality of position and orientation values.

5. The method of claim 1, further comprising calculating a distortion indicator at each individual frequency in the range of the available transmitter frequencies.

6. The method of claim 1, further comprising continuing operation of the electromagnetic tracking system using the set of optimal transmitter frequencies that correspond to the lowest distortion indicator levels.

7. The method of claim 1, further comprising continuously calculating a distortion indicator arbitrarily changing the transmitter frequency, and calculating a distortion indicator at each individual transmitter frequency.

8. The method of claim 1, further comprising using only those position and orientation values that are below an acceptable range or below a predetermined threshold value for determining and visualizing the position and orientation of an object being tracked by the electromagnetic tracking system.

9. A method of improving the distortion tolerance of an electromagnetic tracking system, the method comprising:
   using a plurality of different coil combinations to calculate a plurality of position and orientation values;
   using a computing device to calculate a distortion indicator;
   comparing the distortion indicator to the differences between the plurality of position and orientation values; and
   using an optimizing technique to change the operating conditions of the electromagnetic tracking system when the distortion indicator is greater than a predetermined threshold value to reduce the differences between the plurality of position and orientation values.

10. A method of improving the distortion tolerance of an electromagnetic tracking system, the method comprising:
    using a plurality of different transmitter frequencies and a computing device to determine a set of optimal transmitter frequencies in real-time for use by the electromagnetic tracking system; and
    using the set of optimal transmitter frequencies to reduce the distortion caused by a distorter within the tracking volume.

11. A method of improving the distortion tolerance of an electromagnetic tracking system, the method comprising:
    using a plurality of different transmitter frequencies and a computing device to calculate a plurality of position and orientation values;
    using the computing device to compare permutations of the plurality of position and orientation values to determine differences between the plurality of position and orientation values; and
    using an optimizing technique to change the operating conditions of the electromagnetic tracking system to reduce the differences between the plurality of position and orientation values.

12. The method of claim 11, further comprising calculating a distortion indicator at each individual transmitter frequency.

13. The method of claim 12, wherein the system continues operation using the set of transmitter frequencies that correspond to the lowest distortion indicator levels.

14. The method of claim 12, wherein the distortion indicator is calculated continuously and the frequency set is changed arbitrarily or based on a preset pattern within an available frequency range whenever the distortion indicator is greater than a predetermined threshold value until a usable frequency set is found.

15. The method of claim 12, wherein the distortion indicator can be calculated for each frequency or frequency set in use at the same time, and the solution tied to the best distortion indicator level can be selected for use each time.

16. The method of claim 12, wherein the distortion indicator is recomputed based on a subset of the solution set after removing one or more position and orientation solutions from the solution set based on an alternative indicator, such as having all but one of the solutions close in agreement, resulting in the one being removed.

17. The method of claim 11, wherein multiple transmitter frequencies can be used for each coil concurrently.

18. A method of improving the distortion tolerance of an electromagnetic tracking system, the method comprising:
    using a plurality of different coil combinations to calculate a plurality of position and orientation values;
    using a computing device to analyze the plurality of position and orientation values to determine differences between the plurality of position and orientation values; and
    removing a particular coil or coils from a coil set to reduce the level of disagreement between the plurality of position and orientation values when there are multiple position and orientation values from the set and a particular coil or coils is used repeatedly in position and orientation values that are above an acceptable range of position and orientation values or above a predetermined threshold value.

19. The method of claim 18, further comprising ramping through an available range of transmitter frequencies to determine a set of optimal transmitter frequencies to reduce the differences between the plurality of position and orientation values.

* * * * *

UNITED STATES PATENT AND TRADEMARK OFFICE
CERTIFICATE OF CORRECTION

PATENT NO.         : 7,912,662 B2                                     Page 1 of 3
APPLICATION NO.    : 11/859946
DATED              : March 22, 2011
INVENTOR(S)        : Joel Frederick Zuhars et al.

It is certified that error appears in the above-identified patent and that said Letters Patent is hereby corrected as shown below:

In the drawings, Sheet 2, Fig. 2, please delete "241" and replace with --211--. See attached
In the drawings, Sheet 4, Fig. 4, please insert a dashed arrow from step 424 to step 404. See attached
In Column 9, line 28, please delete "?" and replace with --.--.
In Column 9, line 30, please delete "nor" and replace with --or--.
In Column 10, line 25, please delete "300" and replace with --400--.
In Column 10, line 60, please delete "?" and replace with --.--.
In Column 10, line 62, please delete "nor" and replace with --or--.
In Column 11, lines 11-12, please delete "by electromagnetic the tracking system" and replace with --by the electromagnetic tracking system--.
In Column 11, line 43, please delete "?" and replace with --.--.
In Column 11, line 45, please delete "nor" and replace with --or--.
In Column 11, line 51, please delete "then add" and replace with --then, at step 422, add--.
In Column 11, line 54, please delete "frequencies while" and replace with --frequencies, at step 424, while--.

Signed and Sealed this
Fifteenth Day of November, 2011

David J. Kappos
*Director of the United States Patent and Trademark Office*